United States Patent [19]

Haber et al.

[11] Patent Number: 4,838,870

[45] Date of Patent: Jun. 13, 1989

[54] REMOVABLE NEEDLE ATTACHMENT HAVING A DETACHABLE NEEDLE

[75] Inventors: Terry M. Haber, Lake Forest, Calif.; Jack E. Maze, St. Louis, Mo.; Roger R. Crouse, De Land, Fla.

[73] Assignee: Sherwood Medical Co., St. Louis, Mo. ; a part interest

[21] Appl. No.: 59,498

[22] Filed: Jun. 8, 1987

[51] Int. Cl.[4] .............................................. A61M 5/325
[52] U.S. Cl. ....................................... 604/187; 604/264
[58] Field of Search .......................... 604/110, 164–170, 604/192–198, 264, 283, 187

[56] References Cited

U.S. PATENT DOCUMENTS

| | | | |
|---|---|---|---|
| 2,667,872 | 2/1954 | Smith | 604/192 |
| 4,675,005 | 6/1987 | DeLuccia | 604/110 |
| 4,710,170 | 12/1987 | Haber et al. | 604/195 |
| 4,747,829 | 5/1988 | Jacob et al. | 604/110 |
| 4,747,830 | 5/1988 | Gloyer et al. | 604/110 |

*Primary Examiner*—C. Fred Rosenbaum
*Assistant Examiner*—Mark F. Colosimo
*Attorney, Agent, or Firm*—Morland C. Fischer

[57] ABSTRACT

A needle attachment to be removably attached to the distal end of a syringe cylinder. The needle attachment comprises a needle carrying hub and a coaxially aligned hypodermic needle which is retained by friction within a hole extending through the hub. The needle includes a needle stop to prevent the detachment of the needle from the hub in a distal direction through the hole. The needle terminates at a needle catch that is spaced inwardly from the distal end of the cylinder. A piston assembly having a needle capturing receptacle located at one end thereof moves axially and distally through the syringe cylinder to expulse fluid medication and to selectively engage the needle catch of the hypodermic needle at the most distal aspect of the cylinder. The piston assembly is then moved axially and proximally through the syringe cylinder to detach the hypodermic needle from the needle carrying hub and relocate said needle from the distal end to a relatively proximal position within the cylinder. The needle extends from the piston assembly with the needle catch securely anchored within the needle capturing receptacle and the needle cannula completely surrounded and shielded by the cylinder. Accordingly, the syringe may be safely disposed of without having to either handle or destroy the needle.

15 Claims, 1 Drawing Sheet

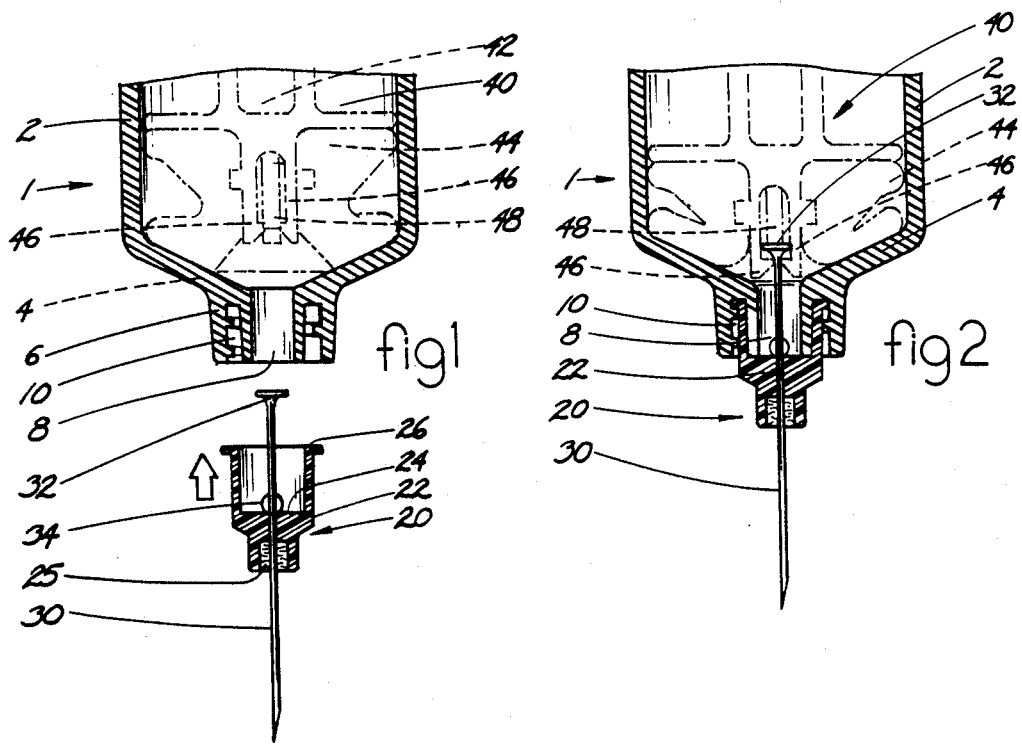
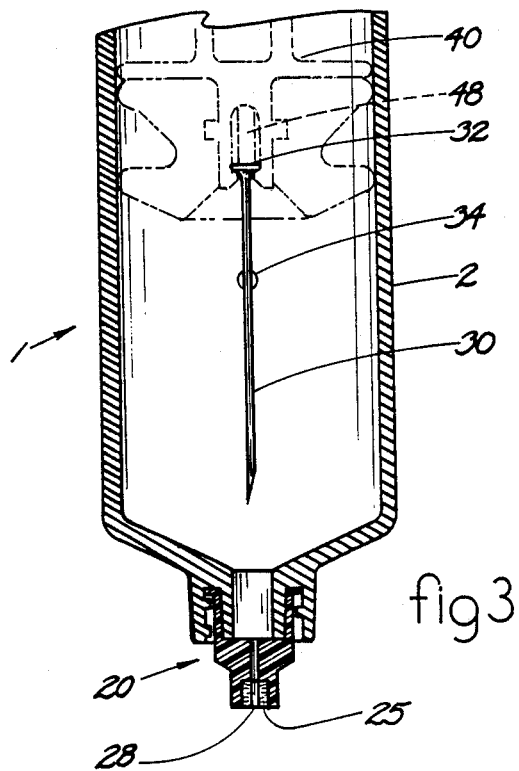

REMOVABLE NEEDLE ATTACHMENT HAVING A DETACHABLE NEEDLE

BACKGROUND OF THE INVENTION

1. Field of the Invention

This invention relates to a needle attachment to be removably attached to the distal end of a syringe cylinder for supporting a hypodermic needle which may be selectively detached from the needle attachment and relocated from the distal cylinder end to a relatively proximal position within the cylinder, so that a used syringe may be disposed of without having to handle or destroy the needle.

2. Prior Art

Hypodermic syringes are used for a variety of injection procedures including the delivery of medicinal drugs to a recipient. However, once the injection procedure is completed and the syringe cylinder emptied, problems may arise as a consequence of failing to properly and adequately dispose of the syringe. By way of a first example, the syringe may be used to treat a patient having a communicable disease. To prevent reuse, the hypodermic needle is sometimes broken before the syringe is discarded. Health care workers are susceptible to accidental and potentially infectious needle strikes due to the careless handling of the hypodermic needle when breaking the needle or disposing of the syringe after use. The resulting mini-accidents caused by an accidental needle strike typically require a blood test for such diseases as AIDS and hepatitis. The corresponding cost and inefficiency of testing health care workers who have received an inadvertent needle strike result in considerable waste, which may be particularly damaging to a health care facility striving for economy and efficiency.

The following U.S. Pat. Nos. provide examples of syringes having a hypodermic needle which may be withdrawn into the syringe cylinder after use:

2,722,215 Nov. 1, 1955
4,026,287 May 31, 1977
4,507,117 Mar. 26,1985

However, in none of the aforementioned patents is there disclosed a hypodermic needle carrying attachment which may be removably attached to the distal end of a syringe cylinder for supporting a hypodermic needle therefrom, so that the needle may be removed from the syringe along with the needle attachment, or the needle may be detached from the needle attachment and relocated from the distal end to a relatively proximal position within the syringe cylinder. Moreover, none of the aforementioned patents shows a syringe assembly having a needle attachment which is adapted to be efficiently and effectively used in a double needle technique, where a first needle, by which the syringe cylinder is infused with a fluid medication, is replaced by a second needle by which the medication is injected from the syringe to the patient. Any reasonable attempt to use the aforementioned syringes in such a double needle technique will likely, and undesirably, necessitate the increased handling of the hypodermic needle which may adversely impact sterility or increase the chance for an accidental needle strike and the spread of contagious diseases.

SUMMARY OF THE INVENTION

Briefly, a needle attachment is disclosed to be removably attached to the distal end of the cylinder of a syringe. The needle attachment comprises a needle carrying hub and a coaxially aligned hypodermic needle which is retained by friction within a hole formed through the hub. The needle includes an integral needle stop which is larger than the diameter of the hole in the needle carrying hub to prevent the detachment of the needle from the hub in a distal direction through the hole. A cutting end of the needle projects outwardly from the distal cylinder end. The opposite end of the needle terminates at a needle catch that is spaced inwardly from the distal cylinder end.

The syringe includes a piston assembly that is adapted for reciprocal and axial movement through the cylinder. The piston preferably comprises an elongated stem and an elastomeric seal attached to one end thereof. The seal functions as a plunger head when the piston assembly is moved through the cylinder for filling the cylinder with fluid medication during an infusing procedure or expulsing medication from the cylinder during an injection procedure. Located at the center of the seal is a needle capturing receptacle. When the piston assembly is moved distally through the syringe cylinder during an injection of medication, the needle capturing receptacle is axially advanced into engagement with the needle catch at the most distal aspect of the cylinder. The piston assembly is then moved proximally through the syringe cylinder, whereby to detach the needle from the hub of the needle attachment and relocate the needle from the distal cylinder end to a relatively proximal position within the cylinder. Accordingly, the syringe may be safely discarded after use without requiring the handling or destroying of the needle, inasmuch as the needle cannula is retracted within the syringe cylinder to be surrounded and rendered irretrievable therewithin.

BRIEF DESCRIPTION OF THE DRAWINGS

FIG. 1 is a cross-section showing the distal end of a syringe cylinder and the needle attachment of the present invention to be removably attached thereto;

FIG. 2 is the cross-section of FIG. 1 showing the needle attachment affixed to the distal end of the syringe cylinder and a piston assembly engaging a hypodermic needle at the most distal aspect of the cylinder; and FIG. 3 shows the cross-section of FIG. 1 with the hypodermic needle detached from the needle attachment and removed, by the piston assembly, from the distal end of the cylinder to a relatively proximal position within the cylinder.

DESCRIPTION OF THE PREFERRED EMBODIMENT

The needle attachment of the present invention and the syringe to which such attachment is connected are best described while referring to the drawings. In FIG. 1, there is shown a syringe 1 comprising a barrel or cylinder 2. The cylinder 2 has an open proximal end (not shown) and a substantially closed distal end wall 4. Projecting outwardly from distal end wall 4 is a relatively narrow neck 6. A hole is formed through neck 6 to define a distal bore 8. An annular receptacle 10 is formed in neck 6 around the periphery of distal bore 8. Receptacle 10 is threaded, so that the soon to be described needle attachment 20 may be removably attached to the distal end of syringe 1 in a manner that will be described in greater detail while referring to FIG. 2.

The needle attachment 20 of the present invention comprises a hollow needle carrying hub 22. Hub 22 has an open proximal end and a substantially closed distal end 24. A flange 26 extends around the open proximal end of hub 22. A narrow, longitudinally extending hole (designated 28 and best shown in FIG. 3) is formed through the distal end 24 of hub 22. The hole 28 is particularly sized to accommodate a hypodermic needle 30 therethrough, whereby a secure friction fit is formed therebetween. A small chamber 25 is formed in the distal end 24 of hub 22. A fibrous material (e.g. cotton, gauze, or the like) may be located within chamber 25 to trap any blood removed from the patient when needle 30 is detached proximally from the hub 22, in a manner which will soon be described.

The needle 30 is detachably connected to and coaxially aligned with the hub 22 of needle attachment 20, so that an outwardly extending cutting end of needle 30 is accessible for penetrating either a sealed container, so that the syringe cylinder 2 can be infused with a fluid medication, or the skin of a patient, so that the fluid medication can be injected from the cylinder 2. The opposite end of needle 30 extends proximally from hub 22 and terminates at a relatively large needle catch 32. Coextensively formed with needle 30 is a needle stop 34. The needle stop 34 is located at approximately the mid-point of needle 30, although the precise location of stop 30 is not to be considered a limitation of this invention. Needle stop 34 may be an integral bump, dimple, ferrule, or any other extension of needle 30 which increases the diameter thereof. As an important feature of the present invention, the needle stop 34 abuts the distal end 24 of the hub 22 to prevent the axial advancement and block the distal detachment of needle 30 from hub 22 via the hole 28 therein. That is to say, the needle stop 34 provides needle 30 with a diameter which is larger than that of the hole 28 formed through hub 22. Therefore, the needle 30 cannot be detached from the needle attachment 20 in a distally oriented direction. However, as will soon become apparent, the needle 30 may be detached from needle attachment 20 in a proximally oriented direction.

Located at the interior of syringe cylinder 2 is a piston assembly (shown in phantom and represented by the reference numeral 40) which is adapted for reciprocal and axial movement through cylinder 2. By way of particular example, a suitable piston assembly, which has application to the present invention, is disclosed in co-pending patent application Ser. No. 25,419 filed Mar. 13, 1987 by Terry M. Haber et al, the content of which application is incorporated herein by this reference. While the aforementioned piston assembly 40 is preferred, it is, of course, to be understood that the actual piston assembly employed does not constitute a limitation of the invention claimed herein.

Briefly, however, the preferred piston assembly 40 comprises an elongated piston stem 42 connected to an elastomeric seal 44. Seal 44 functions as a plunger head when the piston assembly 40 is moved axially through the cylinder 2 of the syringe 1 during a fluid injection procedure. The seal 44 is mounted around a plurality of flexible legs 46 which are spaced from one another to define a needle capturing receptacle 48 therebetween. The operation of piston assembly 40 for detaching the needle 30 from needle attachment 20 will be disclosed in greater detail hereinafter when referring to FIGS. 2 and 3 of the drawings.

Referring now to FIG. 2 of the drawings, the needle attachment 20 is removably attached to the distal end of syringe cylinder 2, such that hypodermic needle 30 extends through distal bore 8 for communication with the interior of cylinder 2. More particularly, the flange 26 at the proximal end of needle carrying hub 22 is received at and rotated around the threaded receptacle 10 within the neck 6 of cylinder 2. In the assembled relationship of FIG. 2, with needle attachment 20 received within receptacle 10 and hypodermic needle 30 extending through distal bore 8, the needle catch 32 of needle 30 is spaced proximally from the distal bore 8 at the most distal aspect of cylinder 2.

The needle attachment 20 described above may be known to those skilled in the art as a Luer lock. Thus, needle attachment 20 may be quickly and easily attached to the distal end of syringe cylinder 2 by simply rotating the needle carrying hub 22 into engagement with threaded receptacle 10, as previously indicated. The hypodermic needle 30 then penetrates a sealed container of fluid medication (not shown), and the piston assembly 40 is moved proximally through cylinder 2 for infusing the cylinder with a supply of such medication. Once the cylinder 2 is infused with fluid medication, it may be desirable to replace the original hypodermic needle with a new, sterile needle. Such a procedure is sometimes known as a double needle technique. Accordingly, the needle attachment (or Luer lock) 20 is removed from syringe 1 by rotating needle carrying hub 22 out of engagement with the threaded receptacle 10. This needle attachment is then discarded, and a new attachment 20 is rotated onto the distal end of syringe 1.

While a Luer lock-type needle attachment 20 has been shown and described, it is to be understood that the needle carrying hub 22 may be releasably attached to the syringe cylinder 2 by any other conventional locking means, including, but not limited to, a bayonet-type connection, a snap-fit connection, a pressure-fit connection, and the like.

After the syringe cylinder 2 is infused with fluid medication, the piston assembly 40 is moved axially and distally through the cylinder 2 to expulse fluid therefrom during a conventional injection procedure. When the piston assembly 40 is moved completely through the cylinder 2, at the conclusion of the injection procedure, the elastomeric seal 44 is compressed against the distal end wall 4, such that the flexible legs 46 of piston assembly 40 are axially advanced into engagement with the needle catch 32 of hypodermic needle 30. The needle catch 32 is thereby snapped into receipt by the needle capturing receptacle 48 formed between legs 46.

Referring now to FIG. 3 of the drawings, the piston assembly 40 is again moved axially and proximally through the syringe cylinder 2, whereby to relocate the hypodermic needle 30 from the hole 28 at the distal end of syringe 1 to a proximal position within cylinder 2. While the needle stop 34 prevents the detachment of needle 30 from the needle attachment 20 in response to a distally directed axial force, the needle 30 may, otherwise, be detached from attachment 20 and retracted into cylinder 2 in response to a proximally directed axial force provided by piston assembly 40. Hence, the needle 30 extends from the piston assembly 40 with the cannula thereof extending through the interior of the cylinder 2 and the needle catch 32 thereof securely anchored within needle capturing receptacle 48.

The syringe 1 may then be discarded in a normal fashion. However, by virtue of the present invention, the syringe is rendered safe by relocating the needle 30 within the syringe cylinder 2, so that the needle is completely shielded by and rendered irretrievable therewithin. Accordingly, neither the syringe 1 nor the hypodermic needle 30 thereof can be reused. Moreover, the used syringe is in a condition to permit safe disposal without requiring handling or cutting of the needle as has heretofore been necessitated as a consequence of many needle assemblies.

It will be apparent that while a preferred embodiment of the present invention has been shown and described, various modifications and changes may be made without departing from the true spirit and scope of the invention. For example, it may be appreciated that the present syringe configuration is adapted to minimize manufacturing and assembly costs, because the hypodermic needle need not be loaded through the syringe cylinder for attachment to the distal end wall thereof.

Having thus set forth a preferred embodiment of the invention, what is claimed is:

1. For a syringe including a cylinder having distal and proximal ends and a piston assembly movable axially and reciprocally through said cylinder, the improvement of a needle attachment to be attached to or removed from the distal end of said cylinder from a location at the exterior of said cylinder, said needle attachment releasably engaging a hypodermic needle so that said needle is attached to or removed from said syringe along with said needle attachment when said needle attachment is attached to or removed from said cylinder, said needle attachment being attached to said cylinder, such that one end of said needle projects outwardly from the distal end of said cylinder and the opposite end of said needle projects inwardly from the distal end of said cylinder, said piston assembly having means by which to engage the opposite end of said needle at the interior of said cylinder for detaching said needle from said needle attachment and removing said needle from said distal end for relocation to a relatively proximal position within said cylinder when said piston assembly is moved towards said proximal cylinder end.

2. The improvement recited in claim 1, wherein said needle attachment and the distal end of said syringe cylinder have respective locking means by which to removably attach said needle attachment to said distal end.

3. The improvement recited in claim 1, wherein said needle attachment comprises a hub having a narrow hole for receiving said needle therethrough, said needle being retained within the hole of said hub by means of a friction fit.

4. The improvement recited in claim 3 wherein said needle includes a needle stop, said needle stop being larger than the diameter of the hole in said hub to prevent the detachment of said needle from said hub in a distal direction through said hole.

5. The improvement recited in claim 1, wherein the opposite end of said needle has a needle catch formed thereat, said needle catch being larger than the diameter of said needle.

6. The improvement recited in claim 5, wherein said piston assembly has a needle capturing receptacle formed at one end thereof for engaging the needle catch of said needle at the most distal aspect of said cylinder.

7. A syringe comprising:
   a cylinder having proximal and distal ends;
   a needle attachment to be attached to or removed from the distal end of said cylinder;
   a hypodermic needle extending through said needle attachment so that one end of said needle projects outwardly from the distal end of said cylinder and the opposite end projects inwardly from the distal end of said cylinder, said needle being releasably engaged by said needle attachment so as to be removed from said syringe along with said needle attachment when said needle attachment is removed from the distal end of said cylinder; and
   means adapted for axial and reciprocal movement through said cylinder to engage the opposite end of said needle and disengage said needle from said needle attachment for relocating said needle from the distal end of said cylinder to a relatively proximal position within said cylinder, such that said needle is fully retracted therewithin.

8. The syringe recited in claim 7, wherein said means adapted for axial and reciprocal movement through said cylinder is a piston assembly, said piston assembly moving towards the distal end of said cylinder for engaging the opposite end of said needle at the distal end of said cylinder, and said piston assembly moving towards the proximal end of said cylinder for detaching said needle from said needle attachment and retracting said needle within said cylinder.

9. The syringe recited in claim 8, wherein said piston assembly has a needle capturing receptacle formed at an end thereof for engaging the opposite end of said needle at the most distal aspect of said cylinder.

10. The syringe recited in claim 9, wherein the opposite end of said needle terminates at a needle catch to be received in the needle capturing receptacle of said piston assembly, said needle catch being larger than the diameter of said needle.

11. The syringe recited in claim 7, wherein said needle attachment and the distal end of said cylinder have respective locking means by which to removably attach said needle attachment to said syringe at the exterior of said cylinder.

12. The syringe recited in claim 7, wherein said needle attachment comprises a hub having a narrow hole formed therein, said needle extending through said hole and being coaxially aligned with said hub.

13. The syringe recited in claim 12, wherein said needle includes a needle stop, said needle stop being larger than the diameter of the hole in said hub through which said needle extends to prevent the detachment of said needle from said hub in a distal direction through said hole.

14. The syringe recited in claim 1, wherein said needle is frictionally and releasably engaged by said needle attachment.

15. The syringe recited in claim 7, wherein said needle is frictionally and releasably engaged by said needle attachment.

* * * * *